United States Patent
Ley et al.

(10) Patent No.: US 7,218,970 B2
(45) Date of Patent: May 15, 2007

(54) SYSTEM FOR MEDICAL LEAD TUNNELING

(75) Inventors: Gregory R. Ley, Blaine, MN (US); Yongxing Zhang, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 7 days.

(21) Appl. No.: 10/601,271

(22) Filed: Jun. 20, 2003

(65) Prior Publication Data

US 2004/0260370 A1    Dec. 23, 2004

(51) Int. Cl.
*A61N 1/00*    (2006.01)
(52) U.S. Cl. ..................................... 607/116
(58) Field of Classification Search ........... 604/164.05, 604/170.01–170.02, 170.12; 606/185; 607/116–129, 607/2; 600/373–381
See application file for complete search history.

(56) References Cited

U.S. PATENT DOCUMENTS

| | | | | |
|---|---|---|---|---|
| 2,458,305 A * | 1/1949 | Sanders | ...................... | 604/526 |
| 3,871,379 A * | 3/1975 | Clarke | ...................... | 606/148 |
| 4,596,559 A * | 6/1986 | Fleischhacker | ........ | 604/164.05 |
| 5,061,245 A * | 10/1991 | Waldvogel | ............ | 604/170.01 |
| 5,300,106 A | 4/1994 | Dahl et al. | ................... | 607/119 |
| 5,405,337 A | 4/1995 | Maynard | | |
| 5,589,563 A | 12/1996 | Ward et al. | .................... | 528/44 |
| 5,683,447 A | 11/1997 | Bush et al. | ................. | 607/126 |
| 5,690,648 A * | 11/1997 | Fogarty et al. | ............. | 606/129 |
| 5,693,081 A | 12/1997 | Fain et al. | ................... | 907/126 |
| 5,782,841 A | 7/1998 | Ritz et al. | ..................... | 606/129 |
| 5,807,317 A * | 9/1998 | Krech, Jr. | ................... | 604/506 |
| 5,843,031 A * | 12/1998 | Hermann et al. | ........ | 604/95.01 |
| 5,902,331 A * | 5/1999 | Bonner et al. | .............. | 607/122 |
| 5,938,603 A | 8/1999 | Ponzi | | |
| 6,183,485 B1 * | 2/2001 | Thomason et al. | ......... | 606/148 |
| 6,215,231 B1 | 4/2001 | Newnham et al. | | |
| 6,254,568 B1 | 7/2001 | Ponzi | | |
| 6,324,414 B1 | 11/2001 | Gibbons et al. | ............ | 600/373 |
| 6,327,492 B1 | 12/2001 | Lemelson | | |
| 6,332,089 B1 | 12/2001 | Acker et al. | ................ | 600/424 |
| 6,340,588 B1 | 1/2002 | Nova et al. | | |
| 6,348,045 B1 * | 2/2002 | Malonek et al. | ............ | 604/270 |
| 6,360,130 B1 * | 3/2002 | Duysens et al. | ............ | 607/132 |
| 6,436,119 B1 * | 8/2002 | Erb et al. | .................... | 606/198 |

* cited by examiner

*Primary Examiner*—Mark Bockelman
(74) *Attorney, Agent, or Firm*—Schwegman, Lundberg, Woessner, & Kluth, P.A.

(57) ABSTRACT

An apparatus includes an elongated tube and an elongated rod having a holding member on one end, the holding member is adapted to hold an end of a lead such that the end of the lead can be pulled through the elongated tube resulting in minimal forces on the lead.

20 Claims, 3 Drawing Sheets

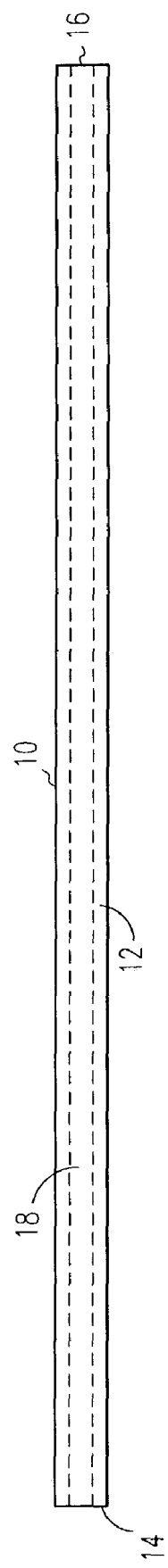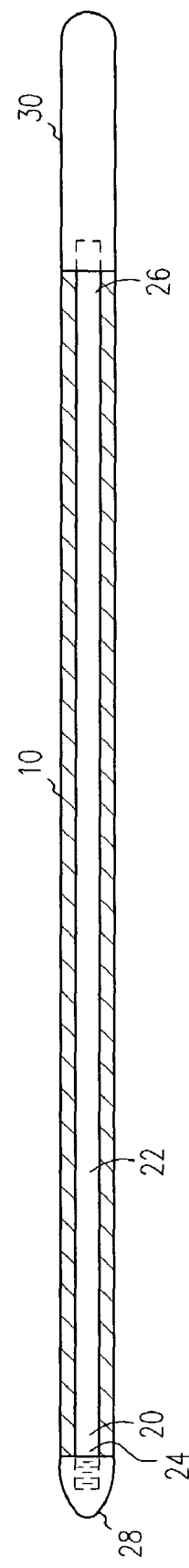
FIG. 1
FIG. 2

SYSTEM FOR MEDICAL LEAD TUNNELING

FIELD OF THE INVENTION

This invention relates to the field of medical devices, and more specifically to a method and apparatus for medical lead tunneling.

BACKGROUND

Medical leads, such as cardiac leads, have a distal end having one or more electrodes and a proximal end having a terminal which is coupled to a pulse generator. Sometimes, subcutaneous tunneling is required to implant the lead. For example, subcutaneous tunneling of the lead can be needed during implantation of epicardial leads, nerve or muscle stimulation leads, or cardiac leads with the pulse generator implanted abdominally. Subcutaneous tunneling is done using a tunneling tool which includes an elongated rod that is inserted through the subcutaneous tissue. After the rod is inserted, a lead terminal holder is attached to the tip of the rod and the lead terminal is attached to the terminal holder. Then the rod is pulled back through the subcutaneous tissue to bring the lead terminal through the tissue to the pulse generator. Subcutaneous lead tunneling can result in high forces on the lead as it is being pulled through the subcutaneous tissue.

SUMMARY

An apparatus includes an elongated tube and an elongated rod having a holding member on one end, the holding member is adapted to hold an end of a lead such that the lead can be pulled through the elongated tube resulting in minimal forces on the lead.

BRIEF DESCRIPTION OF THE DRAWINGS

FIG. 1 shows a side view of a tube in accordance with one embodiment.

FIG. 2 shows a side view of the tube of FIG. 1 mounted to a tunneling tool.

DETAILED DESCRIPTION

Figure 3:
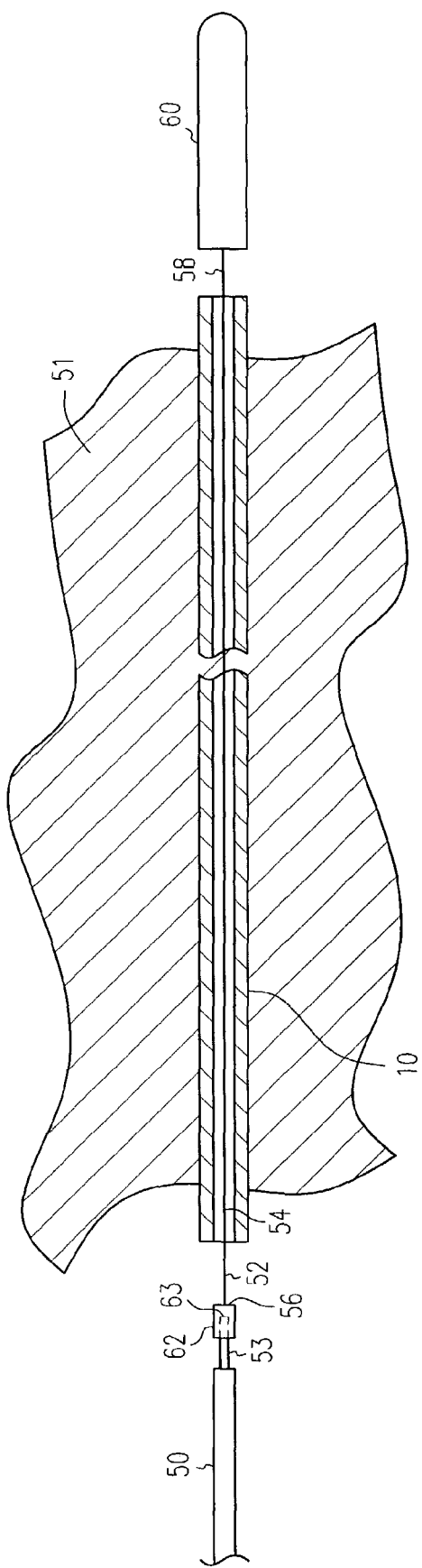
FIG. 3 shows a lead being pulled through the tube of FIG. 1.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

In some embodiments, the present system provides a lead tunneling method and system that allows, for example, subcutaneous lead tunneling for a cardiac pacing or defibrillation lead. In one example, the system can be used to transport a lead subcutaneously from a lead entrance point to a pulse generator implanting site. The lead tunneling system assists in preventing damage to the lead and electrode in the tunneling procedure as the force placed on the lead and electrode is minimized or eliminated.

FIG. 1 shows a side view of a tube 10 used for subcutaneous tunneling, according to one embodiment. Tube 10 includes an elongated, hollow body 12 extending from a first end 14 to a second end 16. Tube 10 is a generally cylindrical tube including an inner bore 18. Tube 10 can be flexible or rigid and can be made of plastic, polymer, Teflon, a metal, such as stainless steel, or a composite material of metal and polymer. In some embodiments, the inside of the tube can be coated to provide less friction. For example, at least a portion of the inner surface of tube 10 can be coated with polyethylene glycol, Teflon, Dow 360 Medical Fluid, or a silicone lubricant. Other examples include a lubricious coating applied by secondary processing such as wet chemistry, plasma deposition, or vapor deposition, for example. When mounted or inserted subcutaneously within a body, tube 10 provides a subcutaneous tunneling path defined by bore 18. This allows an end of a lead to be pulled from first end 14 through the tube and out of second end 16 without undue force being placed on the lead.

FIG. 2 shows tube 10 mounted on a tunneling device 20. Tunneling device 20 is used to insert tube 10 subcutaneously within a patient. Tunneling device 20 includes a rigid, elongated rod 22 extending from a first end 24 to a second end 26. A tip 28 is mounted to first end 24 and a handle 30 is mounted to second end 26. Tip 28 is for driving the tunneling device through subcutaneous tissue by pushing on handle 30. In one embodiment, tip 28 includes a blunt, cone-shape. In one example, tip 28 is removably mounted to first end 24, by using a threaded attachment, for example. Handle 30 can also be removably attachable to second end 26 using a threaded attachment, for example. The length and diameter of rod 22 can vary depending on the tunneling procedure being done. The tunneling rod 22 is stiff enough to tunnel subcutaneously and, in some examples, can have flexibility to facilitate the curvature of regions of the body where lead tunneling is to be performed. In one embodiment, a tunneling device, such as a Model 6888 Lead Tunneler, by Guidant, can be used.

Tube 10 fits over rod 22 such that rod 22 extends through bore 18 from one end of tube 10 to the other. To place tube 10 onto tunneling device 20, either handle 30 or tip 28 can be removed from its respective end, and the tube is slid over rod 22. The tip or handle is then reattached to the rod.

To insert tube 10 subcutaneously, tube 10 is placed onto rod 22. Tip 28 is pushed into and through the tissue until the tip exits the tissue at the proper point. When the tube is properly placed, tip 28 or handle 30 can be removed from rod 22 and the rod can be pulled out of tube 10, which then defines a subcutaneous tunnel.

FIG. 3 shows a lead 50 before being pulled through tube 10, in accordance with one embodiment. Tube 10 is inserted within body 51 and defines a subcutaneous tunnel through bore 18. Lead 50 is pulled through tube 10 using a lead carrier tool 52. In one embodiment, lead carrier tool 52 includes an elongated body 54 extending from a first end 56 to a second end 58. Elongated body 54 can include a rigid rod or a wire. Second end 58 can include a handle 60. First end 56 includes a lead holding member, such as a gripping member 62 which is adapted to grip and hold an end of lead 50. In one embodiment, gripping member 62 can include a biased clip 63 to provide a gripping force to the outer surfaces of lead terminal 53. In other embodiments, the lead holding member can include spring-biased clips, clamps, or other gripping or holding members.

In one embodiment, rod 22 of tunneling device 20 (FIG. 2) can be used as the lead carrier tool 52. For example tip 28 can be removed from rod 22 (FIG. 2) and a holding member, such as member 62, can be attached in its place.

Referring to FIGS. 1–3, in one example use the present tunneling system can include inserting elongated tube 10 subcutaneously within a body and pulling a lead through the elongated tube. For example, a user chooses an appropriate diameter size tunneling device 20 and tube 10. Tube 10 is mounted to rod 22 and the handle and tip are screwed onto the tunneling device 20. In one embodiment, the tunneling device is tunneled from the lead sight to the pulse generator sight subcutaneously. In some embodiments, the rod can be tunneled from the pulse generator sight to the lead sight. After the device has been tunneled, either the tip or the handle can be unscrewed and the rod can be withdrawn from tube 10. An end of the lead, either the terminal end or the electrode end, is engaged to the holding member 62, which is attached to the lead carrier tool 52 (which can be the tunneling rod 22 or a separate member). The carrier tool 52 is inserted into tube 10 and then pulled through the tube to pull the end of the lead through the tube from one end of the tube to the other. The lead is disengaged from holding member 62 and tube 10 is removed from the patient. The lead is then plugged into a pulse generator. This system minimizes or eliminates tunneling forces on the lead without complicating subcutaneous implantation.

Figure 4:
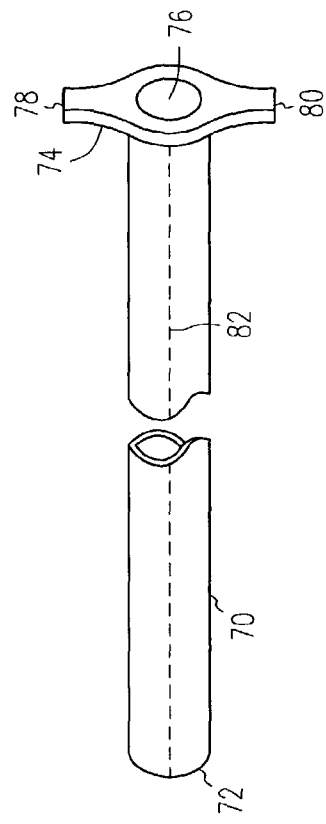
FIG. 4 shows a tube according to one embodiment.

FIG. 4 shows a partial perspective view of a tube 70 in accordance with one embodiment. Tube 70 includes an elongate, hollow body extending from a first end 72 to a second end 74 and includes an internal bore 76. Tube 70 includes a peel-away structure allowing the tube to be split after being inserted subcutaneously. For example, one embodiment includes one or more tabs 78, 80 extending from the tube. One embodiment includes one or more scored or weakened sections 82 running longitudinally along the tube body. In use, tube 70 can be inserted subcutaneously as discussed above. After a lead has been pulled through the tube, tabs 78 and 80 can be grabbed and pulled apart to split the tube body to remove the tube. Such a peel-away structure is useful, for example, if a portion of the lead (for example a terminal) is larger than the bore of the tube. Accordingly, in one example the lead can be pulled through the tube by the electrode end from end 74 to end 72 with the larger terminal end remaining outside end 74. The tabs 78, 80 are then pulled apart to split the tube and the tube is removed.

Figure 5:
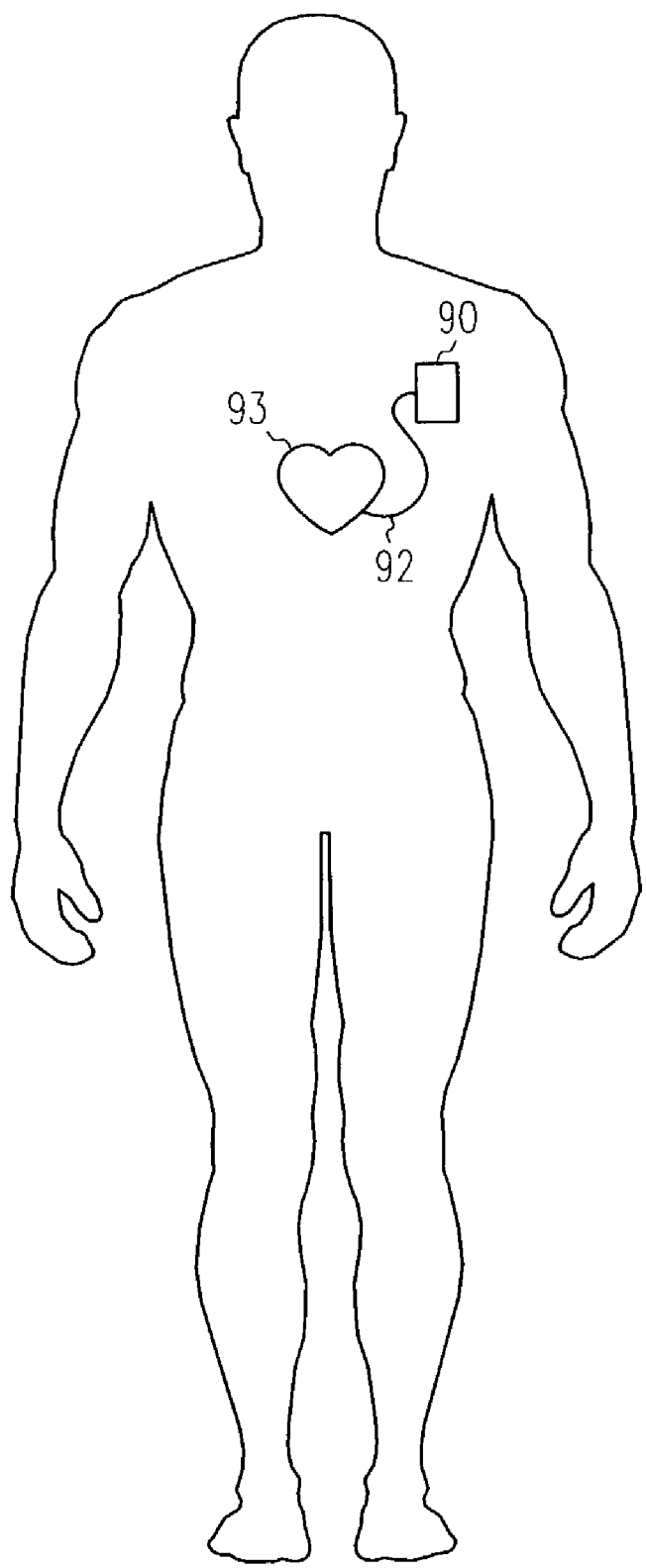
FIG. 5 shows an implanted pulse generator and a lead implanted subcutaneously in accordance with one embodiment.

FIG. 5 illustrates one of the applications for the present system. For example, one application includes an implantable pulse generator 90 such as a pacemaker, defibrillator or a cardiac resynchronization therapy device. The pulse generator 90 is coupled with a lead system 92. The lead system 92 extends subcutaneously from heart 93 to pulse generator 90. In this example lead 92 is an epicardial lead. Pulse generator 90 can include circuitry such as monitoring circuitry and therapy circuitry. The circuitry is designed to monitor heart activity through one or more of the leads of the lead system. The therapy circuitry can deliver a pulse of energy through one or more of the leads of lead system to the heart, where the medical device 90 operates according to well known and understood principles.

In other examples, the present system allows for subcutaneous implantation for when implanting a lead/electrode for nerve and muscle stimulation. Other embodiments can be used with epicardial lead placement and for myocardial lead placement with the pulse generator abdominally implanted or pectorally implanted. In other embodiments the device can be applicable for sub-muscular or intra-muscular tunneling, or other tunneling through a structure in the body that must be traversed in order to implant a lead.

The present system allows for tunneling leads subcutaneously without imposing undue force on the lead. For example, in one embodiment, the present system protects the lead from damage since the lead is tunneled with reduced or minimal force through the tunneling tube, instead of tunneling directly through the subcutaneous area.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An apparatus comprising:
   an electrode lead;
   an elongated tube including a lubricant-coated internal surface and having a peel-away structure; and
   an elongated rod having a holding member on one end and dimensioned to fit within the elongated tube, the holding member adapted to hold an end of the electrode lead such that the end of the electrode lead can be pulled through the elongated tube.

2. The apparatus of claim 1, wherein the holding member is removably attachable to the elongated rod.

3. The apparatus of claim 1, wherein the elongated tube is flexible.

4. The apparatus of claim 1, wherein the elongated tube is rigid.

5. The apparatus of claim 1, wherein the elongated tube has an internal bore diameter larger than the lead diameter.

6. The apparatus of claim 1, wherein the peel-away structure includes two or more pullable tabs.

7. The apparatus of claim 1, wherein the elongated rod includes a tunneling rod.

8. The apparatus of claim 1, wherein the holding member is adapted to grip a terminal end of the lead.

9. The apparatus of claim 1, wherein the holding member is adapted to grip an electrode end of the lead.

10. The apparatus of claim 1, wherein the holding member includes a biasing portion to engage an outer surface of the lead.

11. A subcutaneous tunneling system comprising:
    an electrode lead;
    an elongated tube;
    a tunneling rod extending from a handle end to a tip end, wherein the elongated tube is mountable around the tunneling rod, the tunneling rod for inserting the elongated tube subcutaneously; and
    a holding member removably attachable to said tunneling rod and adapted to hold an end of the electrode lead to pull the electrode lead through the elongated tube, and an interchangeable tunneling tip removably attachable to said tunneling rod and having generally tapered tip.

12. The system of claim 11, wherein the holding member is removably attachable to the tip end of the tunneling rod.

13. The system of claim 11, wherein the elongated tube includes an internal bore having a diameter dimensioned to be larger than a diameter of the lead.

14. The system of claim 11, wherein the elongated tube is flexible.

15. The system of claim 11, wherein the elongated tube is rigid.

16. The system of claim 11, wherein the elongated tube includes a peel-away structure.

17. An apparatus comprising:
an electrode lead;
an elongated, hollow tube having an inner bore diameter dimensioned to be larger than an outer diameter of the electrode lead, the elongated hollow tube for providing a tunnel within a body; and
an elongated member having a lead holding member on one end and a handle on a second end, the elongated rod dimensioned to fit within the elongated tube such that the lead holding member extends from a first end of the elongated tube and the handle extends from a second end of the elongated tube, the lead holding member adapted to hold an end of the electrode lead located outside the first end of the elongated tube such that the end of the electrode lead can be pulled though the elongated tube to exit on the second end of the elongated tube, a tunneling rod sized to fit in said inner bore and having a tapered tunneling tip having a portion with a larger outer diameter than said bore inner diameter.

18. The apparatus of claim 17, wherein the elongated tube is flexible.

19. The apparatus of claim 17, wherein the elongated tube is rigid.

20. The apparatus of claim 17, wherein the elongated tube includes a peel-away structure.

* * * * *

UNITED STATES PATENT AND TRADEMARK OFFICE
CERTIFICATE OF CORRECTION

| | | |
|---|---|---|
| PATENT NO. | : 7,218,970 B2 | Page 1 of 1 |
| APPLICATION NO. | : 10/601271 | |
| DATED | : May 15, 2007 | |
| INVENTOR(S) | : Ley et al. | |

It is certified that error appears in the above-identified patent and that said Letters Patent is hereby corrected as shown below:

In column 4, line 56, in Claim 11, after "tube" delete "," and insert -- ; --, therefor.

In column 4, line 58, in Claim 11, after "having" insert -- a --.

In column 6, line 2, in Claim 17, delete "though" and insert -- through --, therefor.

Signed and Sealed this

Twenty-fourth Day of July, 2007

JON W. DUDAS
*Director of the United States Patent and Trademark Office*